Aug. 30, 1949. G. MERRILL Plant Pat. 868
PEACH TREE
Filed Aug. 28, 1948
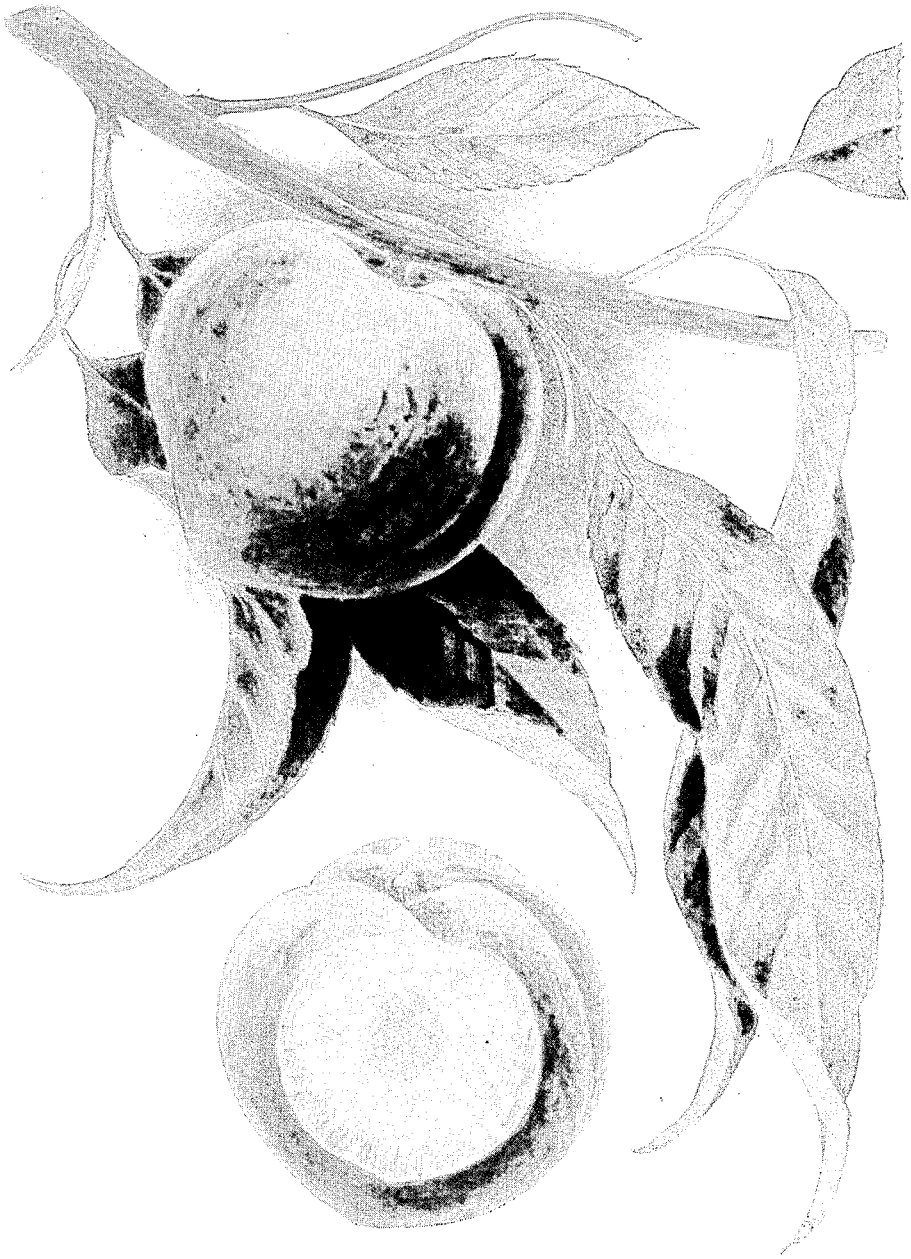
WITNESS
Addison J. Avery
INVENTOR
Grant Merrill
Webster & Webster
ATTYS Patented Aug. 30, 1949

Plant Pat. 868

UNITED STATES PATENT OFFICE

868

PEACH TREE

Grant Merrill, Red Bluff, Calif.

Application August 28, 1948, Serial No. 46,601

1 Claim. (Cl. 47—62)

This invention relates to a new and distinct variety of cling-stone peach tree; the variety being primarily for fresh eating or dessert use.

Included in the advantages of the present variety are the early ripening of the fruit; the large size of the fruit; and the good keeping and excellent shipping qualities thereof. Other advantages will appear hereinafter.

This new and distinct variety of cling-stone peach tree was originated by applicant on his ranch at Red Bluff, California, in the following manner:

Seeds were gathered from a J. H. Hale peach tree growing next to a block of Redbird peaches, and such seeds were planted. One of the resulting peaches resembled the Redbird but was intermediate in ripening between the Redbird and the J. H. Hale. Seeds from this tree, open pollenated, were planted and one of the resulting seedlings, known in the applicant's records as C5–57, was selected as of special merit.

Since its origination the variety has been successfully asexually propagated; having been budded in May 1943 and planted in January 1944. Subsequently, asexually reproduced peach trees of the variety have come into bearing, and are found to retain in full the novel characteristics of the original tree of the variety, and the fruit thereof.

In the original drawings:

Fig. 1 is a perspective view of a fruit of the variety as attached to a twig with leaves.

Fig. 2 is an elevation of the fruit with a portion of the skin and flesh cut away on the near side.

Referring now in detail to the new and distinct variety of peach tree, the following is a detailed description, in outline, of such tree and its fruit:

*Tree*

Large size; vigorous. Intermediate between upright and spreading; intermediate between dense and open. Vase formed; medium productive; fairly regular bearer.

Trunk: Medium stocky; medium shaggy.

Branches: Medium stocky; medium shaggy; brown.

*Lenticels.*—Medium quantity; medium size.

Leaves: Length 4½ to 6 inches, width 1¾ inches; medium size; ovo-lanceolate—tip acuminate. Medium thick; medium green; smooth.

*Margin.*—Finely crenate; glandular at base.

*Petiole.*—Medium short; medium thick.

*Glands.*—Number 2 to 4; medium size; reniform, opposite; green. Position—on base of leaf, and on petiole. Stipules—on new growth, dropping off early.

Flower buds: Medium size; medium length; obtuse shape; free; very pubescent.

Flowers: Dates of first and full bloom—February 21 and March 9, 1947; February 27 and March 17, 1948. Midseason; medium size; medium pink color.

*Fruit*

Maturity when described—eating, ripe. The date of first picking is in the period of June 10th to 15th, and the date of last picking is in the period of June 18th to 23d; both dependent upon climatic conditions.

Size: Variable, large; diameter, axial, 2¾; transverse in suture plane, 2¾; cheek to cheek, 2¾.

Form: Uniform; round, slightly flattened and mostly symmetrical.

Suture: Medium deep, sometimes very deep at base. Has marked depression toward pistil point.

Ventral surface: Lipped toward base.

Lips: Equal.

Cavity: Rounded; elongated in suture plane with suture showing on one side. Depth, ⅜ inch; breadth, ½ inch. Markings—greenish yellow; some show a little red.

Base: Rounded.

Apex: Round; pistil point apical.

Skin: Medium thick; medium tough; not astringent or bitter; tenacious to flesh. Tendency to crack—none. Coloring—yellow under-coloring but almost solid red and maroon, stripes and splashes.

*Down.*—Scant and short.

Flesh:

*Color.*—Yellow, mottled with red throughout, heavier on the sunny side.

*Amygdalin.*—Scant.

*Juice.*—Moderate.

*Texture.*—Firm, crisp to meaty.

*Fibres.*—Few, fine, tender.

*Ripens.*—Evenly.

*Flavor.*—Mild.

*Aroma.*—Pronounced.

*Eating quality.*—Fair.

Stone: Cling; adheres to flesh over entire surface.

*Fibres.*—Short.

*Size.*—Medium.

*Length.*—1⅜ inches.

*Breadth.*—$\frac{15}{16}$ inch.

*Thickness.*—$\frac{15}{16}$ inch.
*Form.*—Oval
*Base.*—Straight.
*Hilum.*—Oval
*Apex.*—Acuminate.
*Sides.*—Equal, curved both sides.
*Surface.*—Irregularly furrowed throughout, ridged throughout, pitted toward base.
*Ridges.*—Rounded throughout.
*Pits.*—Mostly round, some elongated.
*Ventral edge.*—Thin with wing toward base.
*Dorsal edge.*—Narrow, with narrow deep groove to above center.
*Ridges.*—On enther side, interrupted.
*Color.*—Light tan.
*Tendency to split.*—Very slight tendency to split.

The present variety resembles no other peach available for observation except the Redbird, and in comparison ripens in season with, or slightly ahead of, the same. The variety may be further compared with the Redbird as follows:

(*a*) The flesh is yellow instead of white.

(*b*) The bloom is more nearly mid-season than the late bloom of the Redbird.

(*c*) The bloom is of medium size, whereas the Redbird has a large sized bloom.

(*d*) The tree growth has the vigor of the Redbird.

(*e*) The fruit retains the large size of the Redbird and J. H. Hale, and the flesh, although resembling the Redbird, tends to be more crisp rather than rubbery, especially when the fruit from the tree is fresh.

(*f*) The skin is almost entirely covered with red, whereas the Redbird is only splashed with red.

The present variety is a distinct improvement over the Redbird by reason of the following characteristics:

1. The flesh is of yellow color, as desirable.
2. The skin is much more red in color, and therefore more attractive.
3. The variety can withstand a warmer winter because of the aforesaid mid-season blooming period.
4. A more regular and constant bearer.
5. The crisp, less-rubbery flesh.

The present variety has medium resistance to insects and disease.

The tree and its fruit as herein described may vary in slight detail due to climatic and soil conditions under which the variety may be grown.

Having thus described my invention, I claim:

A new and distinct variety of early cling-stone peach tree, being a cross betwen J. H. Hale and Redbird, characterized—in comparison to the latter—by tree growth of equal vigor, an earlier, mid-season blooming period, a smaller bloom, more regular and consistent bearing, and fruit of the large size of the J. H. Hale and Redbird, being yellow fleshed mottled with red, redder in color of skin, and crisper of flesh; the fruit having good keeping quality and an excellent shipping quality.

GRANT MERRILL.

No references cited.